United States Patent [19]

Inoue et al.

[11] Patent Number: 5,066,714
[45] Date of Patent: Nov. 19, 1991

[54] CURABLE ORGANOPOLYSILOXANE PUTTY-LIKE COMPOSITION

[75] Inventors: Yoshio Inoue; Masachika Yoshino, both of Annaka; Hironao Fujiki, Takasaki, all of Japan

[73] Assignee: Shin-Etsu Chemical Co., Ltd., Japan

[21] Appl. No.: 422,206

[22] Filed: Oct. 17, 1989

[30] Foreign Application Priority Data

Oct. 18, 1988 [JP] Japan ................................ 63-262120

[51] Int. Cl.$^5$ ................................................ C08K 5/24
[52] U.S. Cl. .................................... 524/731; 524/267; 524/268
[58] Field of Search ...................... 524/267, 268, 731

[56] References Cited

U.S. PATENT DOCUMENTS 4,293,477 10/1981 Theodore ........................... 524/268

Primary Examiner—Melvyn I. Marquis
Attorney, Agent, or Firm—Lowe, Price, LeBlanc & Becker

[57] ABSTRACT

A curable organopolysiloxane putty-like composition comprising an organopolysiloxane having at least two alkenyl groups in one molecule, an organohydrogenpolysiloxane having at least three $\equiv$SiH groups, a catalytic amount of platinum or a platinum compound, and an inorganic filler. This composition further comprises an organopolysiloxane modified with an alkyl group directly bonded to silicon atoms and having from 7 to 30 carbon atoms whereby the modified organosiloxane serving as an oil properly exudes prior to curing but does not exude appreciably after the curing. The composition is suitable particularly for impressions.

23 Claims, No Drawings

CURABLE ORGANOPOLYSILOXANE PUTTY-LIKE COMPOSITION

BACKGROUND OF THE INVENTION

1. Field of the Invention

This invention relates generally to an impression material and particularly, to a curable organopolysiloxane putty-like composition which is kept putty-like prior to curing by the action of an internal releasing agent. Once the composition has been cured, it becomes useful as an impression material without impeding an appearance or lowering the dimensional accuracy because of a reduced degree of bleeding of the internal release agent. The term "impression material" used herein is intended to mean one which is used, for example, in the dental field as the imprint of the teeth and surrounding tissues for use as a mold in making dentures, or one which is used to imprint the hand. As a matter of course, the putty-like composition may be applied not only as such an impression material, but also for identification and electric insulation.

2. Description of the Prior Art

A variety of curable organopolysiloxane compositions are known in the art. For impression materials, there have been widely used those compositions which comprise organopolysiloxanes having an alkenyl group and organohydogenpolysiloxanes having a hydrogen atom directly bonded to the silicon atom ($\equiv$SiH group) and wherein these siloxane compounds are subjected to addition reaction in the presence of a platinum catalyst.

Putty-like compositions ordinarily used are those which are obtained by internally adding aliphatic hydrocarbon release agents such as, for example, liquid paraffin and white vaseline to the composition of the above type, so that the ingredients do not attach to hands when mixing.

The aliphatic hydrocarbon added as the release agent is allowed to bleed on the putty composition surface prior to curing. This is very advantageous from the viewpoint of handling in that when mixed or kneaded, the putty-like composition does not attach to hands. However, the aliphatic hydrocarbon is caused to gradually bleed out on the surface after the curing, presenting the problems that the appearance of the cured product is worsened and that the size of the cured product after impression differs from that of a matrix.

SUMMARY OF THE INVENTION

It is an object of the invention to provide a curable organopolysiloxane putty-like composition which overcomes the disadvantages of the prior art.

It is another object of the invention to provide a curable organopolysiloxane putty-like composition which comprises, as a release agent, an organopolysiloxane having a predetermined amount of a long-chain alkyl group or groups whereby good working properties are obtained without attachment of the composition to hands during handling and bleedout of the release agent after curing rarely takes place.

The present invention provides a curable organopolysiloxane putty-like composition which comprises: (1) 100 parts by weight of an organopolysiloxane having at least two alkenyl groups in one molecule; (2) an organohydrogenpolysiloxane having at least three $\equiv$SiH groups in one molecule wherein the hydrogen atoms are directly bonded to the respective silicon atoms and used in an amount sufficient to provide 0.5 to 5 times by mole of the $\equiv$SiH groups relative to the alkenyl groups in the ingredient (1); (3) a catalytic amount of platinum or a platinum compound; and (4) from 20 to 600 parts by weight of an inorganic filler. The present invention is characterized in that the putty-like composition further comprises, as ingredient (5), from 5 to 60 parts by weight of an organopolysiloxane having from 5 mole % to 50 mole % of alkyl groups having from 7 to 30 carbon atoms based on the total organic groups bonded to silicon atoms.

The composition comprising the above ingredients (1) to (4) is a known addition reaction-type curable organopolysiloxane composition. It has been found that when the ingredient (5) which is a specific type of organopolysiloxane is added to the known composition as an internal release agent, this release agent is allowed to bleed out on the surface of the composition prior to curing and little bleedout on the surface occurs after the curing.

DETAILED DESCRIPTION AND EMBODIMENTS OF THE INVENTION

The first ingredient used in the composition of the invention is an organopolysiloxane which should have at least two alkenyl groups each bonded to a silicon atom in one molecule. Such organopolysiloxanes are, for example, those of the following formulae

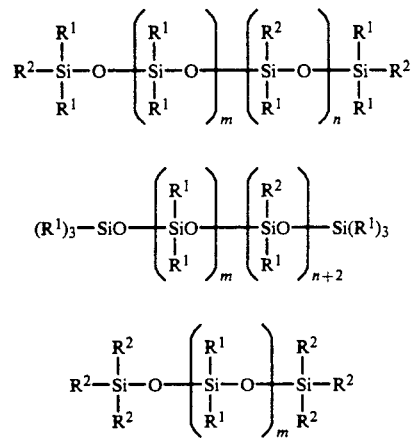

wherein $R^1$'s may be the same or different and represent an unsubstituted or substituted monovalent hydrocarbon group, and $R^2$'s may be the same or different and represent an alkenyl group having from 2 to 4 carbon atoms, m is an integer of from 50 to 100,000, and n is an integer of from 0 to 10,000 provided that $n/m = 0$ to $0.1$.

The unsubstituted or substituted monovalent hydrocarbon group represented by $R^1$ includes an alkyl group having from 1 to 6 carbon atoms, e.g. a methyl group, an ethyl group, a propyl group, a butyl group or the like, an aryl group such as a phenyl group, a tolyl group or the like, or a substituted alkyl or aryl group wherein part or all of the hydrogen atoms of the above groups are substituted with a halogen atom, e.g. a chloromethyl group, a 3,3,3-trifluoropropyl group or the like. Of these, $R^1$ is preferably an alkyl group having from 1 to 4 carbon atoms. More preferably, at least 50 mole % of the total of $R^1$'s should be a methyl group.

Examples of the alkenyl group represented by $R^2$ include a vinyl group, an allyl group, a butenyl group and the like.

The organohydrogenpolysiloxane used as the second ingredient acts, as a crosslinking agent, on the first organopolysiloxane ingredient and should have at least three hydrogen atoms directly bonded to the respective silicon atoms ($\equiv$SiH groups) in the molecule. The organohydrogenpolysiloxane is of the following average unit formula $$H_a R_b^1 SiO_{[4-(a+b)]/2}$$

wherein $R^1$ has the same meaning as defined with respect to the first ingredient, $0.01 \leq a \leq 1$, preferably $0.02 \leq a < 1$, and $1.6 \leq b \leq 2$, preferably $1.8 \leq b \leq 2$, provided that $1.8 \leq a+b < 3$, preferably $1.95 \leq a+b \leq 2.95$. Moreover, the organohydrogenpolysiloxane should preferably have from 3 to 500, preferably from 3 to 300 silicon atoms in the molecule and may be linear, branched or cyclic in structure.

In order to permit good miscibility with the first ingredient, the second ingredient should preferably have a molecular weight lower than the first ingredient. The organopolysiloxane is used in such a way that the $\equiv$SiH groups are provided in amounts of 0.5 to 5 times by mole the alkenyl groups in the first organopolysiloxane ingredient. If the amount is less than 0.5 times by mole, the addition reaction does not proceed satisfactorily. On the other hand, if the amount is over 5 times by mole, the resultant product becomes brittle and excess $\equiv$SiH groups will be left in the final product, causing the product to be degraded as time passes.

The third ingredient is platinum or a platinum compound which may be any known compound ordinarily used as a catalyst for the addition reaction. Examples of the third ingredient include platinum black or platinum supported on silica, carbon black or the like, chloroplatinic acid, an alcohol solution of chloroplatinic acid, complex salts of chloroplatinic acid, olefins and vinylsiloxane, and the like. The amount is preferably in the range of from 0.0001 to 0.1 part by weight per 100 parts by weight of the total of the first and second ingredients.

The inorganic filler used as the fourth ingredient may be any material ordinarily used for this type of organopolysiloxane composition. Examples of such material include finely divided silica such as fumed silica, precipitated silica and the like, quartz powder, glass fibers, carbon powder, iron oxide, titanium oxide, zinc oxide, calcium carbonate, magnesium carbonate and the like. The amount of the inorganic filler is in the range of from 20 to 600 parts by weight, preferably from 50 to 400 parts by weight, per 100 parts by weight of the first ingredient of the alkenyl group-containing organopolysiloxane. If the amount is less than 20 parts by weight, the resultant putty-like composition becomes so soft that it is difficult to handle. If the amount is over 600 parts by weight, the composition becomes too hard to handle as well.

The fifth ingredient is an organopolysiloxane which is added as an internal release agent. This compound should have from 5 to 50 mole %, preferably from 10 to 50 mole %, of alkyl groups having from 7 to 30 carbon atoms, preferably from 8 to 18 carbon atoms, based on the total of organic groups bonded to the silicon atoms. Preferably, the organopolysiloxane is a linear diorganopolysiloxane. Preferable examples include those compounds of the following formulae

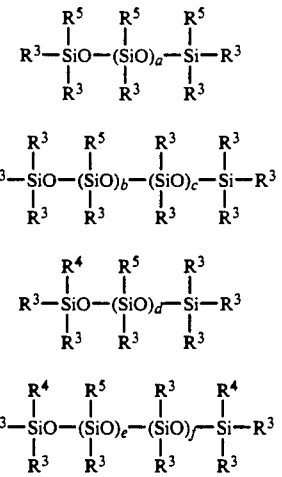

In the above formulae, $R^3$ and $R^4$ have, respectively, the same meanings as $R^1$ and $R^2$ defined in the first ingredient, $R^5$ represents an alkyl group having from 7 to 30 carbon atoms, a is an integer wherein $0 \leq a < 10,000$, preferably $1 \leq a < 5,000$, b and c are, respectively, an integer wherein $1 \leq b < 10,000$, $0 \leq c < 10,000$ and $1 \leq b+c < 10,000$ provided that $0 \leq c/b < 9$, d is an integer wherein $1 \leq d < 10,000$, preferably $1 \leq d < 5,000$, and e and f are, respectively, an integer wherein $1 \leq e < 10,000$, $0 \leq f < 10,000$ and $1 \leq e+f < 10,000$ provided that $0 \leq f/e < 9$. $R^3$'s and $R^4$'s may be, respectively, the same or different. Preferably, each $R^3$ is a methyl group, and each $R^3$ is a methyl group and each $R^4$ is a vinyl group. Moreover, it is also preferred that each $R^3$ is a methyl group, each $R^4$ is a vinyl group, and $R^5$ is an alkyl group having from 8 to 18 carbon atoms in the respective formulae.

More preferably, those compounds of the following formulae are used as the fifth ingredient

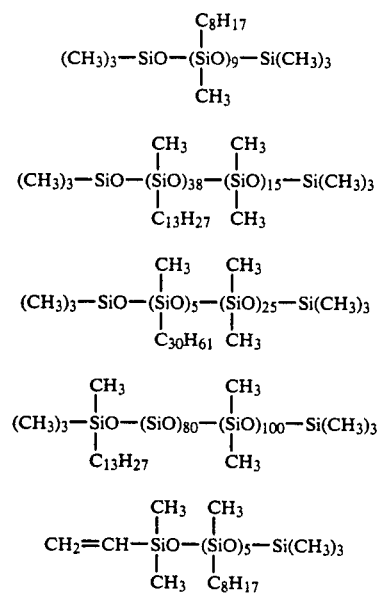

When the degree of polymerization of the organosiloxane exceeds 10,000, the resultant composition becomes so viscous that its bleedout on the surface prior to curing does not proceed smoothly. On the other hand, if the degree of polymerization is less than 2, the bleedout after curing takes place excessively. Accordingly, the degree of polymerization is in the range of from 2 to 10,000, preferably from 3 to 5,000.

If the amount of the fifth ingredient is less than 5 parts by weight per 100 parts by weight of the first ingredient, a satisfactory releasing effect cannot be expected. If the amount is over 60 parts by weight, exudation from the putty-like composition is in excess. Thus, the amount ranges from 5 to 60 parts by weight.

The alkyl modification for the fifth ingredient is carried out by addition reaction between an organohydrogenpolysiloxane, for example, of the following formula

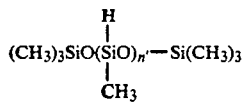

and an α-olefin compound, for example, of the formula, $CH_2=CH(CH_2)_{m'}-CH_3$, in the presence of platinum or a platinum compound under heating conditions to obtain the alkyl-modified compound of the formula,

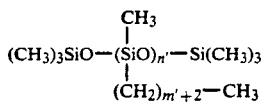

The curable organopolysiloxane composition of the invention is readily obtained by mixing predetermined amounts of the first to fifth ingredients. When stored, it is desirable to provide a two-part system including liquid A wherein a platinum-based catalyst is added to the first alkenyl group-containing polysiloxane ingredient but the second organohydrogenpolysiloxane is not added, and liquid B wherein the second organohydrogenpolysiloxane ingredient is added to the first ingredient but the third platinum-based catalyst is not added. The fourth and fifth ingredients may be added to either liquid A or liquid B, or added to both liquids A and B. If necessary, in order to suppress the activity of the platinum-based catalyst, various organic nitrogen compounds, organic phosphorus compounds and acetylene compounds may be added to the composition. In addition, pigments, dyes and/or perfumes may be added, if desired.

Since the composition of the invention comprises the alkyl-modified siloxane as the fifth ingredient, the liquids A and B can be readily mixed or kneaded when used. After curing, the alkyl-modified siloxane does not exude as readily as liquid paraffin, enabling one to make a precise impression and to make it easy to color the impressed surface. Accordingly, the composition of the invention is useful as an impression for the human body such as an impression of the teeth or hand, and is especially useful when cured articles after completion of impressions are long preserved. Moreover, the composition may have wide utility as impressions for a vertical face or bodies and for identification and electric insulation.

The present invention is described in more detail by way of examples. Synthetic and comparative examples are also described.

SYNTHETIC EXAMPLE 100 g of an SiH group-containing siloxane of the formula,

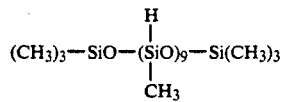

and 1 g of an alcohol solution of chloroplatinic acid having a Pt content of 2 wt % were placed in a 500 ml three-necked flask equipped with a condenser and heated to 80° C. While agitating with a magnetic stirrer, 200 g of $CH_2=CH(CH_2)_5CH_3$ was dropped through a dropping funnel in about two hours. Thereafter, the mixture was heated to 100° C., followed by agitation for further two hours to complete the reaction. At this time, it was confirmed that no SiH group was left. The resultant reaction product was cooled down to room temperature, into which 1.5 g of activated carbon was charged and mixed at room temperature for 2 hours, followed by filtration to remove the platinum. The reaction product was heated under reduced pressure at 200° C./5 mmHg for 3 hours to remove unreacted $CH_2=CH(CH_2)_5CH_3$ therefrom, thereby obtaining a long-chain alkyl-modified compound of the following average composition

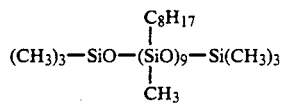

The product had a viscosity of 100 centistokes and a refractive index of 1.45.

EXAMPLE 1

80 parts by weight of a dimethylpolysiloxane oil blocked with a dimethylvinylsiloxy group at both ends of the molecular chain and having a viscosity of 2,500 centistokes (hereinafter referred to simply as vinylsiloxane oil), 20 parts by weight of a dimethylpolysiloxane raw rubber having a viscosity of 1,000,000 poises, blocked with a dimethylvinylsiloxy group at both ends of the molecular chain and having a content of the vinyl group of 0.012 mole % (hereinafter referred to simply as siloxane raw rubber), 0.3 parts by weight of an octyl alcohol-modified solution of chloroplatinic acid (having a Pt content of 1 wt % and hereinafter referred to simply as platinum catalyst), 180 parts by weight of quartz powder having an average size of 4 μm, and 30 parts by weight of an alkyl-modified siloxane oil of the following average formula obtained in the Synthetic Example (hereinafter referred to simply as modified siloxane oil)

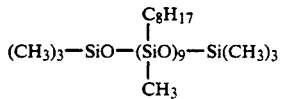

were uniformly mixed by the use of an agitator to obtain putty A.

On the other hand, 75 parts by weight of the vinyl siloxane oil, 20 parts by weight of the siloxane raw rubber, 5 parts by weight of methylhydrogenpolysiloxane blocked with a dimethylhydrogensiloxy group at both ends of the molecular chain and having 17 mole % of methylhydrogensiloxane units (hereinafter referred to simply as H siloxane), 180 parts by weight of the quartz powder, 20 parts by weight of diatomaceous earth and 30 parts by weight of the modified siloxane oil were similarly mixed by means of an agitator to obtain putty B.

Putties A and B were provided in equal amounts and mixed by hands, followed by curing at 60° C. for 1 hour. The cured product was allowed to stand for 1 month but no exudation of the modified siloxane oil was observed.

COMPARATIVE EXAMPLE 1

In the same manner as in Example 1, 80 parts by weight of the vinyl siloxane oil, 20 parts by weight of the siloxane raw rubber, 0.3 parts by weight of the platinum catalyst, 180 parts by weight of the quartz powder, 20 parts by weight of diatomaceous earth, and 30 parts by weight of liquid paraffin were uniformly mixed by the use of an agitator to obtain putty A-1.

On the other hand, 75 parts of the vinyl siloxane oil, 20 parts by weight of the siloxane raw rubber, 5 parts by weight of the H siloxane, 180 parts by weight of the quartz powder, 20 parts by weight of diatomaceous earth and 30 parts by weight of liquid paraffin were similarly mixed by means of an agitator to obtain putty B-1.

The putties A-1 and B-1 were provided in equal amounts and mixed by hands, followed by curing at 60° C. for 1 hour. The cured product was allowed to stand for 3 days but excessive exudation of the liquid paraffin was observed.

EXAMPLES 2 TO 5 AND COMPARATIVE EXAMPLE 2

The general procedure of Example 1 was repeated except that the modified siloxane oil was replaced by the following four modified siloxane oils (Examples 2 to 5) obtained in the same manner as in Synthetic Example and a methylphenylsiloxane oil of the formula indicated below (Comparative Example 2) and each composition was cured at 60° C. for 1 hour and that in Example 5, the H-siloxane compounded in the putty B was used in an amount of 15 parts by weight.

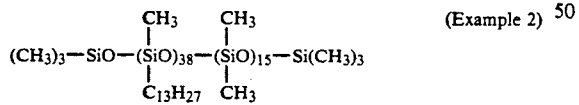 (Example 2)

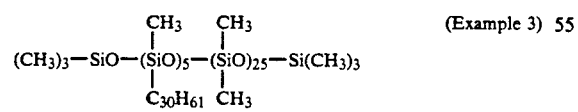 (Example 3)

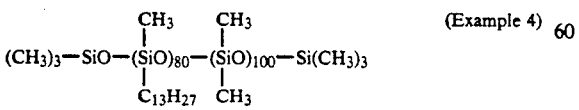 (Example 4)

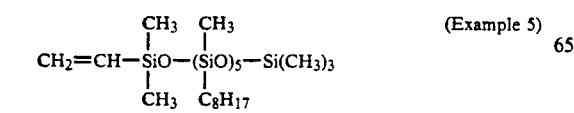 (Example 5)

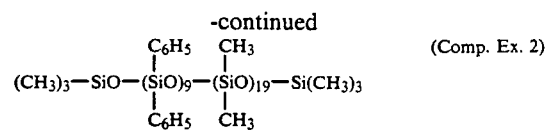 (Comp. Ex. 2)

The respective cured products were each allowed to stand at room temperature for 1 month. As a result, it was found that the products of Examples 2 to 5 involved no exudation of the oil. With the composition of Comparative Example 2, the mixture became a sticky paste, not giving a putty.

What is claimed is:

1. A curable organopolysiloxane putty-like composition which comprises:
   (1) 100 parts by weight of an organopolysiloxane having at least two alkenyl groups in one molecule;
   (2) an organohydrogenpolysiloxane having at least three ≡SiH groups in one molecule wherein the hydrogen atoms are directly bonded to the respective silicon atoms and used in an amount sufficient to provide 0.5 to 5 times by mole of the ≡SiH groups relative to the alkenyl groups in the ingredient (1);
   (3) a catalytic amount of platinum or a platinum compound;
   (4) from 20 to 600 parts by weight of an inorganic filler; and
   (5) from 5 to 60 parts by weight of an organopolysiloxane having from 5 to 50 mole % of alkyl groups having from 7 to 30 carbon atoms based on the total organic groups bonded to silicon atoms.

2. The putty-like composition according to claim 1, wherein the alkenyl-containing organopolysiloxane is of the following formula

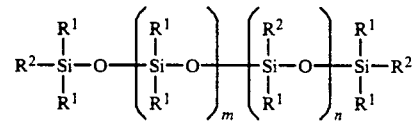

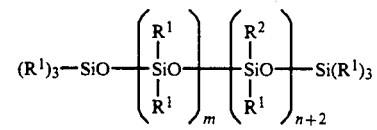

or

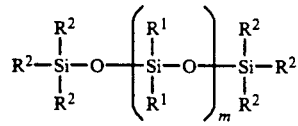

wherein $R^1$'s may be the same or different and represent an unsubstituted or substituted monovalent hydrocarbon group, and $R^2$'s may be the same or different and represent an alkenyl group having from 2 to 4 carbon atoms, m is an integer of from 50 to 100,000, and n is an integer of from 0 to 10,000 provided that $n/m = 0$ to $0.1$.

3. The putty-like composition according to claim 2, wherein each $R^1$ represents an alkyl group having from 1 to 4 carbon atoms.

4. The putty-like composition according to claim 2, wherein at least 50 mole % of the total of $R^1$'s is a methyl group.

5. The putty-like composition according to claim 1, wherein the organohydrogenpolysiloxane of the ingredient (2) has a molecular weight smaller than the organopolysiloxane of the ingredient (1).

6. The putty-like composition according to claim 1, wherein said organopolysiloxane of the ingredient (5) is a linear diorganopolysiloxane.

7. The putty-like composition according to claim 1, wherein said organopolysiloxane of the ingredient (5) has a degree of polymerization of from 2 to 10,000.

8. The putty-like composition according to claim 7, wherein the degree of polymerization is in the range of from 3 to 5,000.

9. The putty-like composition according to claim 1, wherein said organopolysiloxane of the ingredient (5) is of the following general formula

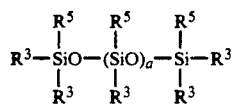

wherein $R^3$'s may be the same or different and represent an unsubstituted or substituted monovalent hydrocarbon group, $R^5$ represents an alkyl group having from 7 to 30 carbon atoms, and a is an integer wherein $0 \leq a < 10,000$.

10. The putty-like composition according to claim 9, wherein each $R^3$ is a methyl group, $R^5$ represents an alkyl group having from 8 to 18 carbon atoms, and a is an integer of $1 \leq a < 5,000$.

11. The putty-like composition according to claim 1, wherein said organopolysiloxane of the ingredient (5) is of the following general formula

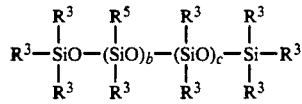

wherein $R^3$'s may be the same or different and represent an unsubstituted or substituted monovalent hydrocarbon group, $R^5$ represents an alkyl group having from 7 to 30 carbon atoms, and b and c are, respectively, an integer wherein $1 \leq b < 10,000$, $0 \leq c < 10,000$ and $1 \leq b + c < 10,000$, provided that $0 \leq c/b < 9$.

12. The putty-like composition according to claim 11, wherein each $R^3$ is a methyl group and $R^5$ represents an alkyl group having from 8 to 18 carbon atoms.

13. The putty-like composition according to claim 1, wherein said organopolysiloxane of the ingredient (5) is of the following general formula

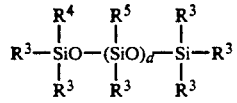

wherein $R^3$'s may be the same or different and represent an unsubstituted or substituted monovalent hydrocarbon group, $R^4$'s may be the same or different and represent an alkenyl group having from 2 to 4 carbon atoms, $R^5$ represents an alkyl group having from 7 to 30 carbon atoms, and d is an integer wherein $0 \leq d < 10,000$.

14. The putty-like composition according to claim 13, wherein each $R^3$ is a methyl group, each $R^4$ is a vinyl group, $R^5$ represents an alkyl group having from 8 to 18 carbon atoms, and d is an integer of $1 \leq d < 5,000$.

15. The putty-like composition according to claim 1, wherein said organopolysiloxane of the ingredient (5) is of the following general formula

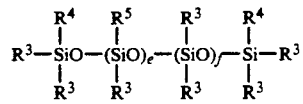

wherein $R^3$'s may be the same or different and represent an unsubstituted or substituted monovalent hydrocarbon group, $R^4$'s may be the same or different and represent an alkenyl group having from 2 to 4 carbon atoms, $R^5$ represents an alkyl group having from 7 to 30 carbon atoms, and e and f are, respectively, an integer wherein $1 \leq e < 10,000$, $0 \leq f < 10,000$ and $1 \leq e + f < 10,000$, provided that $0 \leq f/e < 9$.

16. The putty-like composition according to claim 15, wherein each $R^3$ is a methyl group, each $R^4$ is a vinyl group and $R^5$ represents an alkyl group having from 8 to 18 carbon atoms.

17. The putty-like composition according to claim 1, wherein said organopolysiloxane of the ingredient (5) is of the following formula

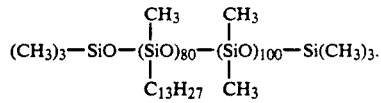

18. The putty-like composition according to claim 1, wherein said composition is made of a two-part system including liquid A made of the ingredients (1) and (3) but free of the ingredient (2) and liquid B made of the ingredients (1) and (2) but free of the ingredient (3).

19. The putty-like composition according to claim 18, wherein the ingredients (4) and (5) are, respectively, added to liquid A and/or B.

20. The putty-like composition according to claim 1, wherein said organopolysiloxane of the ingredient (5) is of the following formula

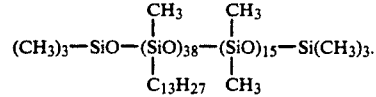

21. The putty-like composition according to claim 1, wherein said organopolysiloxane of the ingredient (5) is of the following formula

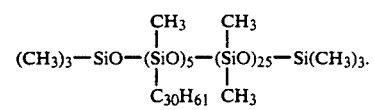

22. The putty-like composition according to claim 1, wherein said organopolysiloxane of the ingredient (5) is of the following formula

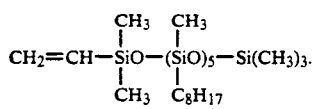
23. The putty-like composition according to claim 1, wherein said organopolysiloxane of the ingredient (5) is of the following formula
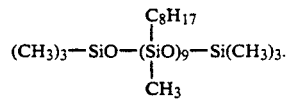
* * * * *